(12) United States Patent
Lin et al.

(10) Patent No.: US 6,699,189 B1
(45) Date of Patent: Mar. 2, 2004

(54) ULTRASOUND DISTORTION COMPENSATION USING BLIND SYSTEM IDENTIFICATION

(75) Inventors: Feng Lin, Waukesha, WI (US); Robert C. Waag, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 10/025,817

(22) Filed: Dec. 26, 2001

Related U.S. Application Data

(60) Provisional application No. 60/257,284, filed on Dec. 26, 2000.

(51) Int. Cl.[7] ................................................ A61B 8/00
(52) U.S. Cl. ...................................................... 600/437
(58) Field of Search ............................... 600/407–471; 73/609–627, 596, 631, 602; 367/7, 11, 87, 130, 138, 95; 128/916

(56) References Cited

U.S. PATENT DOCUMENTS

| | | | | |
|---|---|---|---|---|
| 5,623,928 A | * | 4/1997 | Wright et al. ................ 600/447 |
| 5,793,701 A | * | 8/1998 | Wright et al. .................. 367/7 |
| 6,023,977 A | * | 2/2000 | Langdon et al. .............. 73/629 |
| 6,131,458 A | * | 10/2000 | Langdon et al. .............. 73/627 |
| 6,223,599 B1 | * | 5/2001 | Langdon et al. .............. 73/627 |
| 6,485,423 B2 | * | 11/2002 | Angelsen et al. ........... 600/458 |

* cited by examiner

Primary Examiner—Ali M. Imam
(74) Attorney, Agent, or Firm—Blank Rome LLP

(57) ABSTRACT

Aberrations in ultrasound imaging are modeled as a linear filter bank. The response of each linear filter is determined through blind system identification and is used to correct the aberration by applying a predistortion to the transmit signals and a compensation to the receive signals. To reduce computation, the blind system identification can be done through multiple levels. In a two-level implementation, the transducers in the array are grouped into subapertures. The blind system identification is applied in each of the subapertures to obtain the first-level response to each element. Using these responses, a common input is found for each subaperture, and blind system identification is applied to find the second-level responses. From the first-level and second-level responses, the response at each filter in the bank is determined.

24 Claims, 15 Drawing Sheets

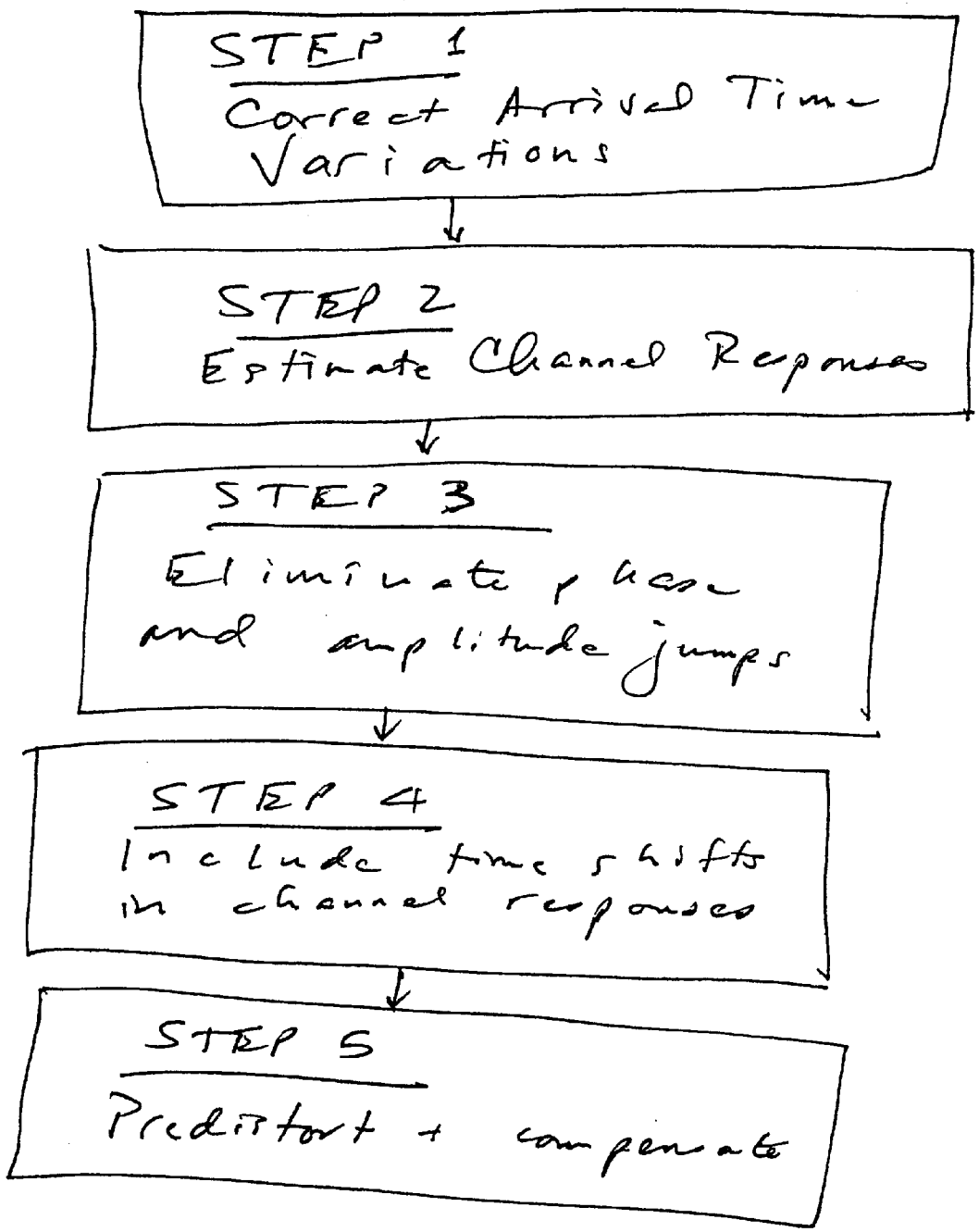

though the output of each path is
known, the signal from the common source is unknown.

ULTRASOUND DISTORTION COMPENSATION USING BLIND SYSTEM IDENTIFICATION

REFERENCE TO RELATED APPLICATION

The present application claims the benefit of U.S. Provisional Application No. 60/257,284, filed Dec. 26, 2000, whose disclosure is hereby incorporated by reference in its entirety into the present disclosure.

STATEMENT OF GOVERNMENT INTEREST

The research leading to the present invention was funded by NIH Grants HL 50855 and CA 74050 and DARPA Grant N00014-96-0749. The government has certain rights in the invention.

FIELD OF THE INVENTION

The present invention is directed to ultrasound imaging and more particularly to a method and apparatus for performing such imaging in which aberrations are estimated and corrected.

DESCRIPTION OF RELATED ART

The use of ultrasound to produce images for medical diagnosis has become common as a result of its nonionizing nature, the ability to produce images resulting from the inherent differences in mechanical properties of various soft tissues, and advances in technology. Current applications include examination of the heart, abdomen, and fetus. In most areas, diagnosis is now generally based on the size, position, contour, and motion of structures as well as on their relative transmission and reflection properties. Although clinical activity continues to expand, present instrumentation using simple geometric focusing is limited by tissue inhomogeneities that produce wavefront distortion. This distortion can degrade geometric focusing to yield images unsatisfactory for accurate diagnosis.

Transmission measurements of wavefront distortion produced by the abdominal wall, breast, and chest wall have been made, as have pulse-echo measurements of ultrasonic distortion produced by the breast and liver. These measurements all indicate that both point resolution, which measures the ability to distinguish between isolated scatterers, and contrast resolution, which measures the distinguishability of speckle patterns and can be more important clinically than point resolution, are severely reduced in many clinical ultrasonic imaging situations.

Wavefront distortion becomes a more serious problem as ultrasonic imaging systems are designed for operation at higher frequencies. This is because excursions in arrival time are larger relative to the wavelength at higher frequencies. These time shifts can significantly reduce the resolution improvement ordinarily associated with focusing at higher ultrasonic frequencies. Therefore, the need for estimation and correction of aberration becomes greater with increasing frequency.

Wavefront distortion can result from arrival time shifts, amplitude variations, and waveform shape changes, among which arrival time shifts may be the most important. Several efforts have been reported to compensate the arrival time shifts. It is known to use cross correlation of signals to estimate arrival time fluctuations and to maximize brightness by adjustment of focus delays. A least-mean-square-error method has been used to estimate the arrival time. In all the above studies, the underlying aberration model is a phase screen in the receiving aperture and only time shifts are taken into account. However, an improved compensation method has been described in which a phase screen is placed at some distance away from the aperture and the estimation of arrival time is made after the wavefronts are backpropagated to the position of the phase screen. This approach is capable of compensating more than time shifts.

Methods based on a single phase screen model are not able to remove aberration completely. First, the aberration is assumed to be introduced by a thin layer, while the thickness of the medium that produces the aberration is generally not negligible in practice. Second, attenuation in tissue is not considered, even though muscle and fat have a frequency dependent attenuation that is, for example, 4.0 dB/cm and 1.7 dB/cm, respectively, at a frequency of 2.6 MHz. Third, propagation through the tissue may produce strong waveform distortion or even multiple pulses that can cause time-shift estimation to fail or cause time shifts to be an inappropriate description of aberration. Simulations of ultrasonic pulse propagation through the abdominal wall and chest wall have shown that weak fluctuation models do not fully describe wavefront distortion.

SUMMARY OF THE INVENTION

In light of the foregoing, it is apparent that a need exists in the art to improve the removal of aberrations. It is therefore an object of the invention to provide an ultrasound imaging technique which does so. It is another object of the invention to improve on the above-noted techniques of the prior art, particularly those based on a single phase screen model.

To achieve the above and other objects, the present invention is directed to a technique for estimation and correction of aberration based on a common random input filter model. In the model, instead of using a phase screen to describe the aberration, the propagation paths are more generally described by a bank of linear filters. The model is capable of including not only time shifts but also amplitude and waveform variations that may also be important components of the distortion. The aberration is described with an accuracy that depends on the number of parameters in each filter rather than any artificial assumption about the nature of the propagation path. After the filter parameters are known, the aberration can be compensated by corresponding inverse filters in beam formation on reception and appropriate time reversal of waveforms for focusing on transmit.

However, the estimation of the linear filter parameters is a challenge because, al
This challenge has attracted the attention of investigators in other fields of endeavor, particularly in the area of communications, where the basic problem often arises and is known as blind system identification (BSI).

In BSI, in the general case where the channels have nonminimum phase, higher-order statistics (HOS) were first used to identify the system because HOS are rich in information. However, inherent difficulties limit the application of HOS. A relatively large number of data samples is required, and the convergence rate is slow. Also, HOS methods may yield a local minimum. Methods based on second-order statistics (SOS) are, thus, preferable. Second-order statistics were found to contain phase information that can be use to recover channel information in the case of cyclostationary signals. However, in this approach, statistical assumptions about the input signal must be made and this is inappropriate particularly when signals are short. Breakthroughs in BSI have recently been made. The cross-relation method provides an algorithm based on SOS for the identification of channels driven by an arbitrary unknown input. That method uses an equality between the output of one channel convolved with the response of another channel and the output of the latter channel convolved with the response of the former channel, a relation for which that approach is named, and necessary and sufficient identifiability conditions are known in terms of the channel characteristics and the input signal. A second step is known that refines the channel estimation by using the channel outputs and initial estimates of filter parameters. This approach is called the two-step maximum likelihood method. An alternative approach is known, called the subspace method. The subspace method is based on the orthogonality of "signal" and "noise" subspaces.

A common random input filter model is used for estimation and correction of wavefront aberration in ultrasonic b-scan imaging. In the model, aberration between the focus and the transducer elements is represented by the response of a linear filter bank to a common random signal. The response of each filter in the bank is found using a two-level extension of an existing subspace method for blind system identification. The received waveforms are compensated using an inverse filter, and the transmit waveforms are predistorted using time reversal.

To test the model, experiments were conducted using a two-dimensional array system to obtain echoes from a point reflector and from a random medium in each case through an aberrator. The aberrator is a phantom that mimics the wavefront distortion produced by a human abdominal wall and the random medium is made to mimic ultrasonic characteristics of a human liver. The results indicate that the method can improve both the transmit and the receive focus and can outperform time-shift estimation and compensation as well as the method of backpropagation followed by time-shift estimation and compensation.

In greater detail, jumps in channel response phase and amplitude that arise in the two-level process were reduced using a least-mean-square-error time-shift estimation method and spatial lowpass filtering. The performance of the estimation was evaluated using a generalized root-mean-square-error metric. Transmit an receive focuses were also evaluated using effective widths, effective radius, and peripheral energy ratio.

The results indicate that the present invention can improve both the receive focus and the transmit focus an that the improvement can be significantly more than what is achieved with single phase screen methods. The results also indicate that, for scattering from a random medium, the transmit focus may require at least partial compensation first by some other technique before the common input assumption is sufficiently valid for the present invention to produce an improved focus.

BRIEF DESCRIPTION OF THE DRAWINGS

A preferred embodiment will be set forth in detail with reference to the drawings, in which:

FIG. 15 shows a flow chart of operational steps for implementing the preferred embodiment.

DETAILED DESCRIPTION OF THE PREFERRED EMBODIMENT

Figure 1:
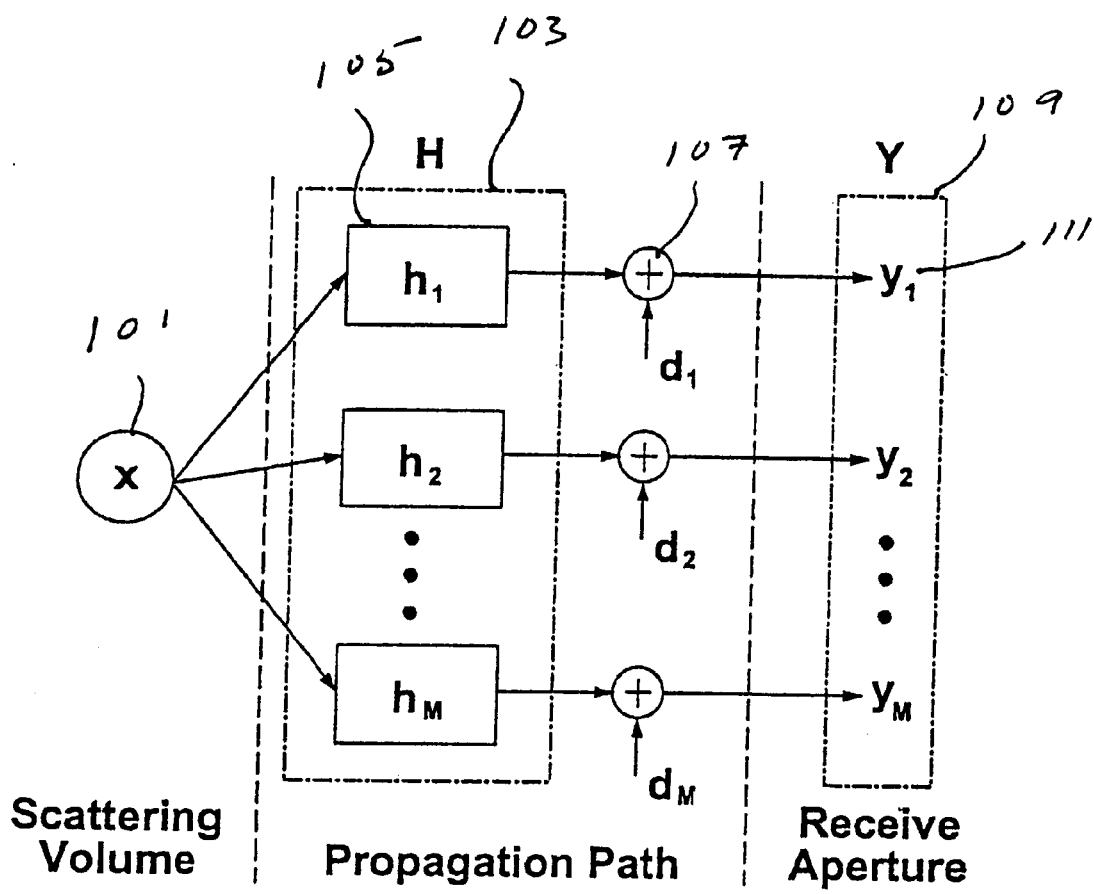
FIG. 1 shows a schematic diagram of a common random input filter model used in the preferred embodiment.

A preferred embodiment and experimental results will now be set forth in detail with reference to the drawings, in which like reference numerals refer to like elements or steps throughout.

Echoes arise when a body of random scatterers is illuminated by a focused beam. These echoes form a wavefront that can be considered random in time and spherical in space. After propagation through an inhomogeneous medium, the wavefront is distorted in both time and space. This distortion contains information about the aberration. Separation of the randomness of the echoes from the effects of the distortion enables calculation and correction of wavefront distortion. This separation is sought through a common random input filter model.

The model is depicted in FIG. 1. As shown in that figure, a common random signal x(t) from a source 101 propagates through a propagation path 103 made up of individual propagation paths 105 modeled as a linear filter bank. Each individual propagation path 105 has a corresponding disturbance $d_m(t)$ 107 which models measurement noise and other deviations of the model from reality. The signals are received in a receive aperture 109 which includes multiple receive elements 111.

Since the beam of illumination is focused, the echoes or scattered signals are modeled as arising from a common effective source 101. Assuming each receive element 111 is associated with an individual propagation path or channel 105, the signal $y_m(t)$ received through channel m is modeled as the output of a linear filter $h_m(t)$ driven by an unknown common random signal x(t). In this model, the randomness of the received signal is represented by the random input, while the propagation effects are represented by the impulse responses of the linear filters. A disturbance $d_m(t)$ is added to the output of each linear filter to account for measurement noise and other deviations of the model from reality. Consequently, the output of the m-th channel is $$y_m(t)=x(t)*h_m(t)+d_m(t). \tag{1}$$

The application of the model to determine the $h_m$s from the $y_m$s is known as blind system identification.

Assuming a tapped delay line or finite impulse response (FIR) structure for the form of the filter that models each channel and assuming the total number of channels is M, the number of available output samples for each of the M channels is N, and the order of each filter is L, the discrete version of Eq. (1) is $$y_m(k) = \sum_{j=0}^{L} h_m(j)x(k-j) + d(k), m = 1, 2, \ldots N. \qquad (2)$$

The above set of equations can be compactly expressed using matrices as $$y = H_M x + d, \qquad (3)$$

where the output vector y is defined as $$y = [y_1^T y_2^T \ldots y_m^T \ldots y_M^T]_{MN \times 1}^T \qquad (4)$$

in which $$y_m = [y_m(1) y_m(2) \ldots y_m(k) \ldots y_m(N)]_{N \times 1}^T, \qquad (5)$$

the noise vector d is defined as $$d = [d_1^T d_2^T \ldots d_m^T \ldots d_M^T]_{MN \times 1}^T, \qquad (6)$$

in which $$d_m = [d_m(1) d_m(2) \ldots d_m(k) \ldots d_m(N)]_{N \times 1}^T, \qquad (7)$$

the common input vector x is defined as $$x = [x(-L) x(-L+1) \ldots x(0) \ldots x(N-1)]_{(N+L) \times 1}^T, \qquad (8)$$

the channel response vector h is defined as $$h = [h_1^T h_2^T \ldots h_m^T \ldots h_M^T]_{M(L+1) \times 1}^T \qquad (9)$$

in which $$h_m = [h_m(0) h_m(1) \ldots h_m(l) \ldots h_m(L)]_{(L+1) \times 1}^T, \qquad (10)$$

and the generalized Sylvester matrix $H_M$ of channel responses is defined as $$H_M = [H_{(1)}^T H_{(2)}^T \ldots H_{(m)}^T \ldots H_{(M)}^T]_{(MN) \times (N+L)}^T \qquad (11)$$

in which $$H_{(m)} = \begin{bmatrix} h_m(L) & h_m(L-1) & \ldots & h_m(0) & 0 & \ldots & 0 \\ 0 & h_m(L) & h_m(L-1) & \ldots & h_m(0) & \ldots & 0 \\ & \ddots & \ddots & \ddots & \ddots & \ddots & \\ 0 & \ldots & 0 & h_m(L) & h_m(L-1) & \ldots & 0 \end{bmatrix} \qquad (12)$$

is the Sylvester matrix of m-th channel response. In these expressions, $(\cdot)(k)$ denotes the k-th sample of a variable, $(\cdot)_m$ is a vector associated with the m-th channel, $(\cdot)^T$ signifies the transpose of a vector or matrix, $(\cdot)_{n \times m}$ indicates size of a vector or matrix, $(\cdot)_{(m)}$ is a matrix constructed from the m-th channel response, $(\cdot)_M$ is a matrix comprised of the response matrix $(\cdot)_{(m)}$ for each of M channels, and the first index of the (causal) common input vector x is assumed for notational convenience to be −L (negative L).

The objective of BSI is to find the channel response vector h from the system output vector y. The calculated channel responses may differ from the actual responses by a common (convolutional) filter response because the model includes any common response in the source. Nevertheless, if the channel order is assumed, the calculated channel responses can be determined uniquely up to a scale factor.

The subspace method that is used as the BSI algorithm in the ultrasonic application of aberration correction is reviewed briefly for convenience below. The signal and noise subspaces whose orthogonality is used in the subspace method are determined from an examination of a covariance matrix defined using Eq. (3). In the absence of noise, this matrix is $$R_y = H^M R_x H_M^H, \qquad (13)$$

where, for an arbitrary vector z, $R_z$ denotes the mathematical expectation of $zz^H$ and $(\cdot)^H$ denotes the Hermitian transpose. The matrix $H_M R_x H_M^H$ has rank N+L if the channel responses have no common zeros, the output sample length N is no less than L, at least one channel has order L, and L is assumed to be known. If the eigenvalues $\lambda_i$, i=0, 1, ..., MN−1, of $R_y$ are ordered from maximum to minimum and their corresponding eigenvectors are denote as $v_i$, the $\lambda_i$ for i=0, 1, ..., N+L−1 are positive and are associated with the signal subspace, while the $\lambda_i$ for i=N+L, ..., MN−1 are all equal to zero and associated with the noise subspace. The noise subspace, the dimension of which is uniquely determined by L, is orthogonal to the signal subspace. This noise space is spanned by columns of $H_M$ i.e., $$V_N^H H_M = 0, \qquad (14)$$

where $$V_N = [v_{N+L} v_{N+L+1} \ldots v_{MN-1}]. \qquad (15)$$

The solution of Eq. (14) yields the channel response vector h for the noise-free case. When noise is present, a least-square-error approach can be used to find a channel response vector h that minimizes $\|V_N^H H_M\|$, where $\|\cdot\|$ denotes the root-mean-square magnitude of a vector. The constraint $\|h\|=1$ in this minimization ensures a unique solution except for a scale factor of ±1.

A direct implementation of the subspace method requires a number of computations that is proportional to the square of the number of channels. Thus, the computational time is long when the number of transducer elements is large. Consequently, direct implementation of the subspace method is not practical for estimation of wavefront distortion when a two-dimensional array transducer with a large number of elements is employed. A two-level BSI method was, therefore, developed to reduce the scale of the computations.

Figure 2:
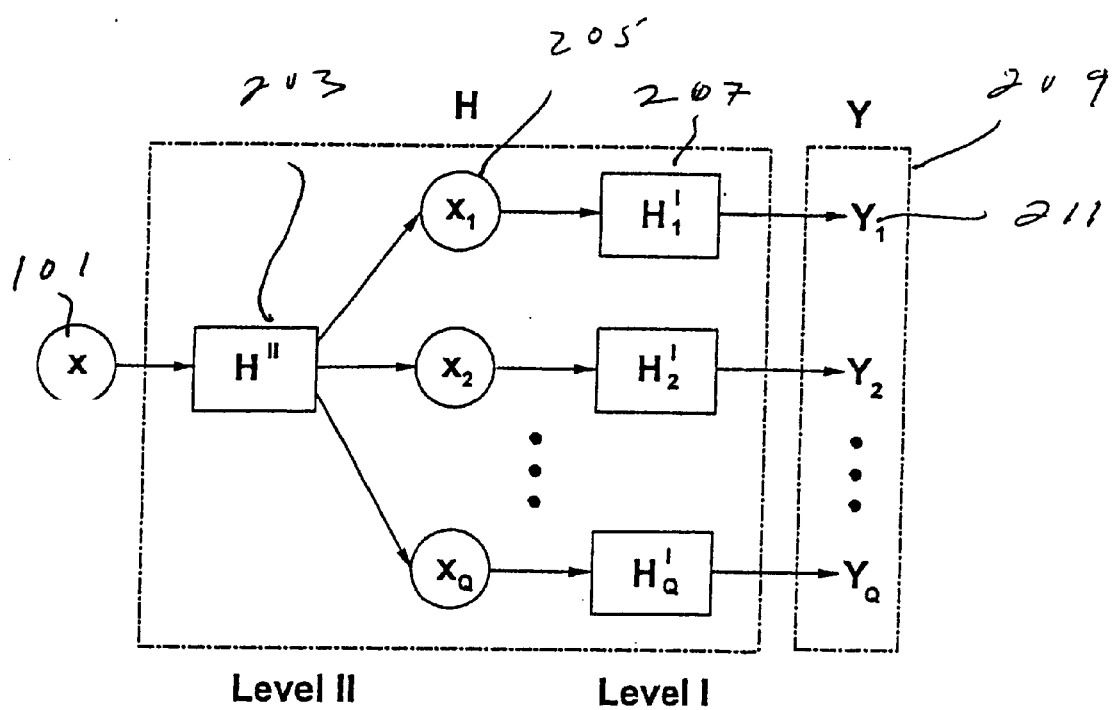
FIG. 2 shows a schematic diagram of a two-level version of the common random input filter model of FIG. 1.

The two-level BSI method uses the model shown in FIG. 2. The receive aperture Y 209 with P×Q elements is divided into Q subapertures 211 $Y_q$, q=1, 2, ..., Q. Each subaperture contains P elements p=1, 2, ..., P. Square subapertures are a natural choice because the basic BSI method assumes a common input and nearby elements may be considered on physical grounds to be excited through paths or channels that have the same input.

The identification is accomplished using two levels. In the first level, the basic BSI approach is applied to find, for each subaperture $Y_q$, the channel responses $H_q^1$ of the channels 207 as well as the input $x_q$ at 205. The channel responses $H_q^1$ contain P FIR filters $h_{pq}^1$ each of which has output $y_{pq}$. In the second level, the channel outputs are comprised of the first-level inputs, $x_q$, and another BSI is made to obtain channel responses $H_q^{11}$ at 203 that contain the FIR filters $h_q^{11}$ each of which has output $x_q$. The desired channel response $h_{pq}$ of each output $y_{pq}$ is then calculated using $$h_{pq} = h_{pq}^1 * h_{pq}^{11}. \qquad (16)$$

Extension of the above two-level method to additional levels will be straightforward to those skilled in the art who have reviewed the present disclosure.

A consequence of the multiple level structure is the presence of phase and amplitude jumps in the estimated channel responses between subapertures. If two channels belong to different subapertures, even though they are close to each other and the channel outputs are similar, the estimated channel responses can have considerably different phases and amplitudes. The jumps are particularly evident in the case of random scattering. Correction of the jumps is necessary to put the estimates for each subaperture on a common basis. Time offsets of subapertures in the two-dimensional array application of interest were eliminated using a least-mean-square-error method. In this method, the time shift between adjacent subapertures is estimated for each side of a subaperture by averaging the time shifts between an element on one side of the subaperture boundary and the adjacent element on the other side of the subaperture boundary. Then, a matrix of relations is formed using $$t_i - t_j = d_{ij},\qquad(17)$$

where $t_i$ and $t_j$ are the time offsets of the adjacent subapertures, and $d_{ij}$ is the time shift between the two subapertures. For a two-dimensional array with K×L subapertures, this approach yields 2KL−K−L equations for the KL time offsets. The overconstrained equations are solved using a Cholsky decomposition and the estimate time offsets are removed from the channel responses. The correction for a one-dimensional array is simpler because the time offsets can be obtained directly from the time shifts between subapertures and no least-mean-square-error estimation is needed. Amplitude jumps in the present application were compensated by spatial lowpass filtering after the alignment of channel responses in time.

The performance of the BSI method can be evaluated using an error metric called here the generalized root-mean-square-error and denoted GRMSE. This metric is defined as $$GRMSE = \sqrt{\min_{h_c(t)} \sum_m \int |\tilde{h}_m(t) * h_c(t) - h_m(t)|^2 dt} \Big/ \sqrt{\sum_m \int h_m^2(t) dt},\qquad(18)$$

where $\tilde{h}_m(t)$ is the estimate, $h_m(t)$ is the true or reference value of the channel responses, and $h_c(t)$ is the impulse response of a common linear filter. A compact form of Eq. (18) is $$GRMSE = \min_{h_c} \|\tilde{H}_M h_c - h\| / \|h\|,$$

where h is the true channel response vector, $h_c$ is a common response vector, and $\tilde{H}_M$ is the generalized Sylvester matrix constructed from the estimated channel response vector $\tilde{h}$.

The response of a common filter $h_c$ is included because, as noted, a frequency dependent amplitude and phase that are the same in each of the channels may be present but are lumped with the common signal in the model used for BSI. This common factor is not, as discussed later, appropriately counted as an error but would affect the error if not included in the metric.

The solution for the minimization in Eq. (19) can be written as $$h_c = (\tilde{H}_M^T \tilde{H}_M)^{-1} \tilde{H}_M^T h.\qquad(20)$$

Consequently, the GRMSE can be expressed as $$GRMSE = \|\tilde{H}_M (\tilde{H}_M^T \tilde{H}_M)^{-1} \tilde{H}_M^T h - h\| / \|h\|.\qquad(21)$$

Figure 14:
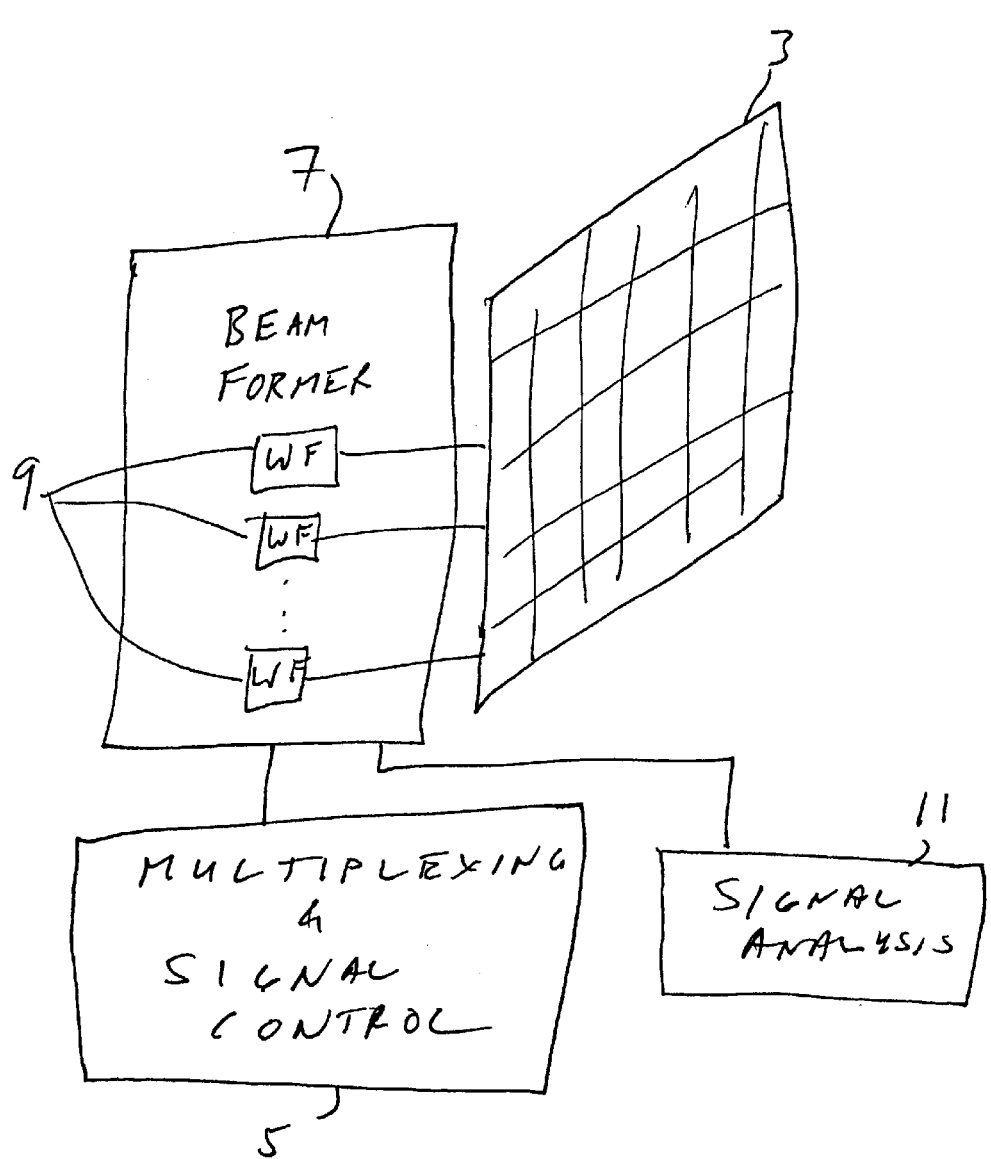
FIG. 14 shows a schematic diagram of an apparatus for implementing the preferred embodiment.

A novel two-dimensional array system employed for measurements in this study is shown in FIG. 14. The apparatus 1 has a two-dimensional 80×80-element transducer array 3 with associated circuitry 5 for multiplexing and signal control and a beam-former 7 with individually programmable transmit waveforms 9. Since the array 3 receives reflected signals, circuitry 11 for signal analysis is also included. The element pitch is 0.6×0.6 mm$^2$. The system has a 3.0 MHz center frequency and a 56% bandwidth. The characteristics of the system permit imaging with an f-number of 1.2 to obtain an isotropic −6 dB resolution of about 0.6 mm in each Cartesian direction. The apparatus 1 can be based on ultrasound equipment presently available from companies such as GE, Siemens, Philips and Toshiba.

Pulse-echo waveforms from a point reflector were acquired to evaluate experimentally the performance of the BSI method when the common source assumption is ideally satisfied. The point reflector was then replaced by a random medium. For the same aberration, the pulse-echo waveforms were acquired under controlled but clinically relevant conditions when the common source is produced by illumination of randomly distributed scatterers. Transmit waveforms emitted from the array propagated through the aberrator to a focus at the point reflector or in the random medium. The reflections propagated back through the aberrator and were received by the array. The receive waveforms were used to estimate the aberration. The estimation was employed to pre-distort the transmit waveforms and to compensate the receive waveforms to improve both the transmit and receive focus.

To measure the transmit focus, the scattering object or medium was removed and focus was scanned using a hydrophone capable of movement in three orthogonal directions by stepper motors so that the focus could be measured in a volume. The measurements using a hydrophone to evaluate BSI in this study were cuts in the x and y directions in the plane of the focus.

The aberrator used in the measurements is a phantom that has first-order and second-order ultrasonic pulse distortion statistics similar to those of human abdominal wall measurements. The phantom is 35 mm thick and has a background made from a fat-mimicking oil-in-gelatin emulsion. Spheres with 6.3 and 12.6 millimeter diameters and made of similar emulsion with different sound speed and density are randomly distributed inside to produce the aberration. The full width at half maximum correlation length and the rms value of the arrival time fluctuations are 7.1 mm and 70.3 ns, respectively, and the corresponding quantities for the energy level fluctuations are 2.4 mm an 3.54 dB, respectively. These statistics are around the high end of the range for corresponding statistics of abdominal wall measurements so the aberration produced by this phantom is considered severe.

The point reflector was the rounded tip of a 0.82 mm diameter stainless steel rod positioned with its axis perpendicular to the plane of the two-dimensional array. The random scattering medium was made to mimic ultrasonic characteristics of human liver; at a temperature of 22° C., the medium has a sound speed of 1.567 mm/$\mu$s and attenuation of 1.27 dB/cm at 2.5 MHz.

In all the measurements set forth in the present disclosure, both transmit and receive f-numbers were 1.2 and the focal point was 55 mm away from the array.

The identification and correction of the aberration can be implemented in a five-step computational procedure, which will be explained with reference to the flow chart of FIG. 15.

Step 1 involves the correction of arrival time variations. Time shift caused by the focal geometry and the aberration is removed from the receive waveform at each element in this step. The purpose is to avoid unnecessarily high filter orders caused by simple time shifts and hence reduce computation. Also, this provides a basis for correction of time jumps between subapertures as described in Step 3 below. The procedure starts with echoes produced in the focal region. The echoes have a spherical delay component. This delay produced by geometric path-length differences is first removed. Then, arrival time fluctuations caused by the aberration are estimated using the least-mean-square-error method. Finally, the arrival time fluctuation is removed to get waveforms that have essentially the same time of arrival.

Step 2 involves the estimation of the channel responses. Channel responses are determined using the previously described two-level implementation of the subspace method. In the first level, the two-dimensional array is divided into square subapertures consisting of 7×7 elements. The BSI method is applied in each subaperture to calculate both the channel responses and the common input. The common input from each of the subapertures is used as an output signal and BSI is performed at the second level. The serial channel responses for each path are then convolved to obtain the total channel responses.

The covariance matrix of the channel outputs is first constructed. Then, the eigenvalues and the eigenvectors of the matrix are calculated and the noise subspace is identified. Finally, the eigenvector associated with the smallest eigenvalue of a matrix defined by the noise subspace is calculated and the elements of this eigenvector are taken as the channel responses. Accurate calculation of the common input of each subaperture in the first level of BSI is an important issue because this signal is used as an output in the second level of BSI. For this calculation, an estimate of the input waveform for each channel in a subaperture was first obtained by deconvolution of the corresponding channel response from the channel output waveform. The deconvolution was implemented in this study by a frequency-domain division confined to the bandwidth of the waveforms to ensure that the processing is stable. Then, the similarity of each calculated input waveform was examined and waveforms significantly different from others were considered to come from a bad channel. Waveform similarity, WS, was quantified by a normalized cross correlation defined as $$WS = \int s_i(t)s_j(t)dt / \sqrt{\int s_i^2(t)dt \int s_j^2(t)dt} \qquad (22)$$

for any two signals $s_i(t)$ and $s_j(t)$. Excluding bad channels, a common input of each subaperture was obtained by averaging the remaining waveforms in the corresponding subaperture, and the average waveforms were then used as outputs in the second level of BSI.

Step 3 involves elimination of phase and amplitude jumps. Time shift between the waveform at an element on one side of a subaperture boundary and the waveform at an adjacent element on the other side of the subaperture boundary was estimated using cross correlation. The time shifts for the element pairs along a subaperture boundary were averaged to obtain an estimate of time shift for the boundary after exclusion of time shifts that were significantly different from others. Then, the previously noted least-mean-square-error method was used with the time shift for each of the subaperture boundaries to get the arrival time for each subaperture. With this arrival time, the offset of each subaperture was removed from all the channel responses in the subaperture.

Using the assumption that the aberration is slowly varying, a two-dimensional spatial lowpass filter was used to smooth the transitions in time shift and amplitude of the channel responses from element to element. First, the time-shift map of the responses was estimated using the noted least-mean-square-error method. The time shifts were next removed from the responses and the spatial lowpass filter was applied to the aligned responses. Then, the time-shifts were also lowpass filtered and added to the channel responses. The lowpass filter used in this study was a Hamming spatial-frequency window with a (one-sided) width of 0.42 cycles/mm.

Step 4 involves inclusion of time shifts in the channel responses. The time shifts caused by the aberration and removed in Step 1 are now included in the channel responses to obtain the final BSI result for each channel filter.

Step 5 involves predistortion of the transmit waveforms and compensation of the receive waveforms. Blind system identification results are used for transmit and receive focus compensation in this step. The channel responses were time reversed to get predistorted transmit waveforms. The predistorted waveforms were emitted and the echoes received. The same channel responses were then deconvolved from the receive waveforms and the resultant waveforms were focused using the assumption of propagation in a homogeneous medium.

The GRMSE given by Eq. (21) was used to quantify error in the estimate channel responses. Reference values of the channel responses were obtained by calculating the channel responses from the point-reflector pulse-echo data obtained through the same aberration. A reference waveform method was used for this calculation. In the method, the reference waveform is the average of the waveforms after time shifts are removed an after exclusion of dissimilar waveforms. Then, the channel responses are deconvolved from the average waveform.

The transmit and receive focus before and after compensation was studied to assess the performance of the method in a different way. The transmit focus was measured with a hydrophone. The receive focus was computed by numerically backpropagating the received waveforms to the focal place. The transmit and receive focuses were quantified using effective widths, effective radius, and peripheral energy ratio (PER). In this procedure, the envelope of the analytic signal at the focus is obtained using a discrete Hilbert transform. Then, a maximum amplitude projection is made in each Cartesian dimension to obtain the effective width that is defined as the width of the projection as a function of level below the peak. The effective radius is half the cube root of the product of the three effective widths as a function of level below the peak. An ellipsoid at a chosen level below the peak is defined for determination of the PER. The center of the ellipsoid is the point of maximum amplitude and the length of each axis is the effective width in the corresponding dimension at the chosen level. The PER is the energy outside the ellipsoid divided by the energy inside the ellipsoid. In the present example, the −10 dB level was chosen for the calculation of the PER.

Figure 3:
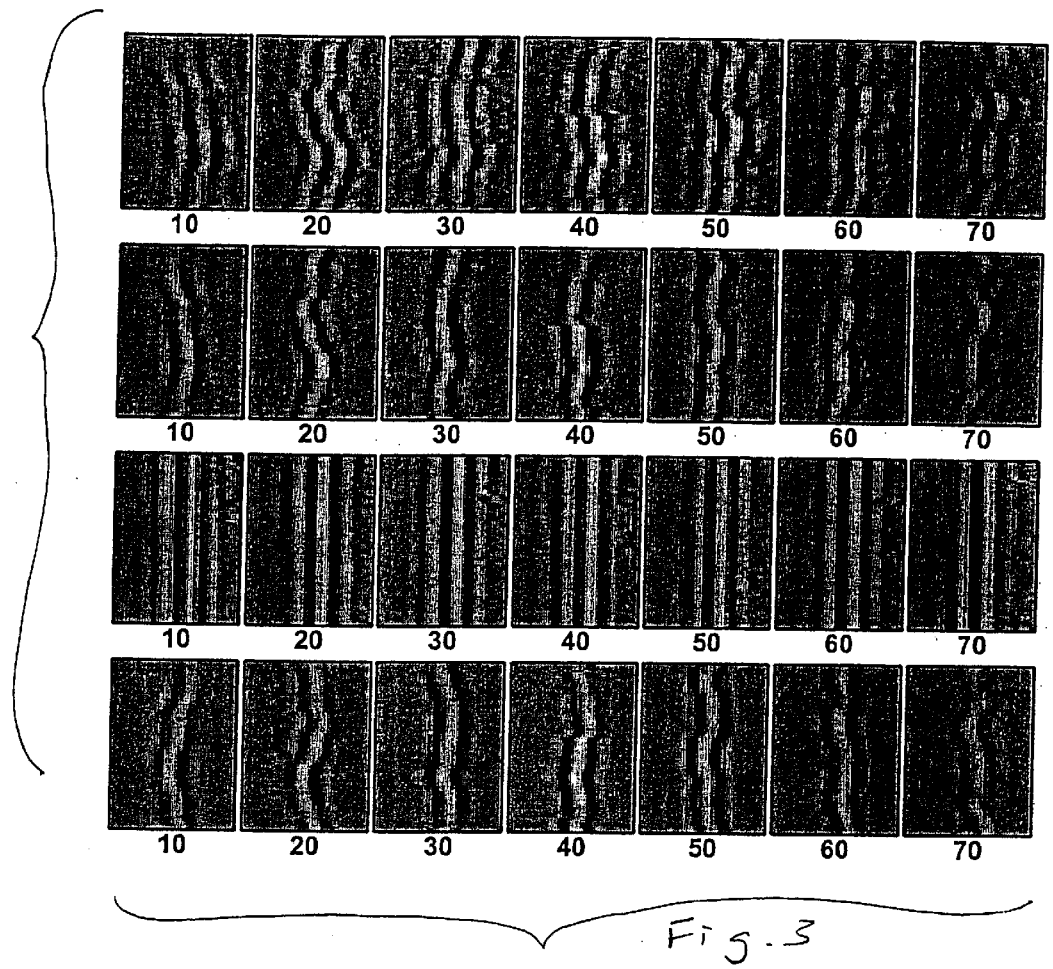
FIG. 3 shows representative aberrated receive waveforms from a point reflector.

Representative aberrated receive waveforms from the point reflector illuminated by a focused beam are shown in the first row of FIG. 3 after correction for geometric path length differences. The root-mean-square (rms) value of the arrival time fluctuation is 75.9 ns and that of energy level variation is 2.8 dB. Channel responses estimated using the BSI method are shown in the second row. As expected, the responses have time shifts an amplitude variations corresponding to those in the receive waveforms. Receive waveforms after compensation using the channel responses obtained from BSI are shown in the third row. The rms arrival time fluctuation and energy level fluctuation of the compensate waveforms are 4.2 ns and 0.7 dB, respectively, values that are much less than the corresponding values before compensation. Predistorted transmit waveforms shown in the fourth row are time-reverse versions of the channel responses. These time-reversed waveforms were used to compensate the distortion caused by the aberrator in the transmit focus.

Figure 4:
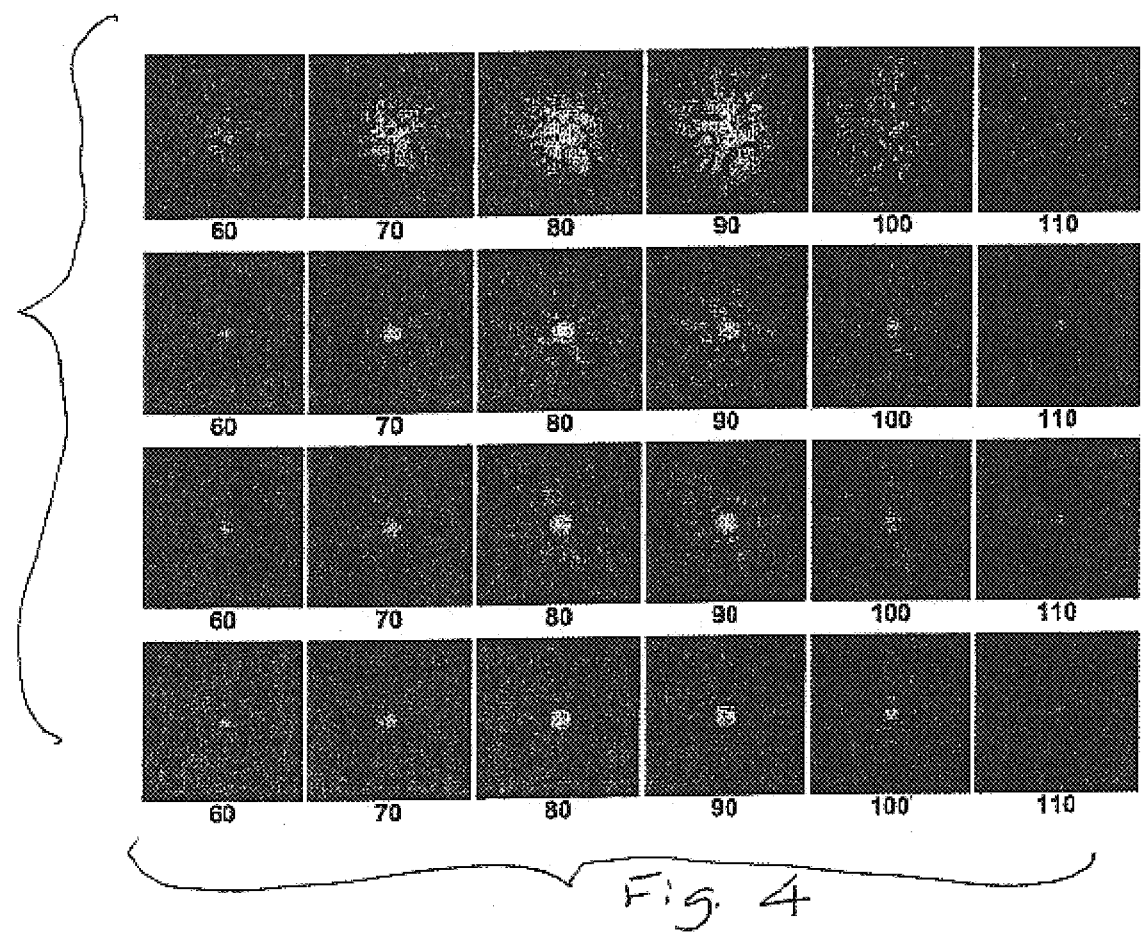
FIG. 4 shows time histories of the receive focus for the point reflector.
Figure 7:
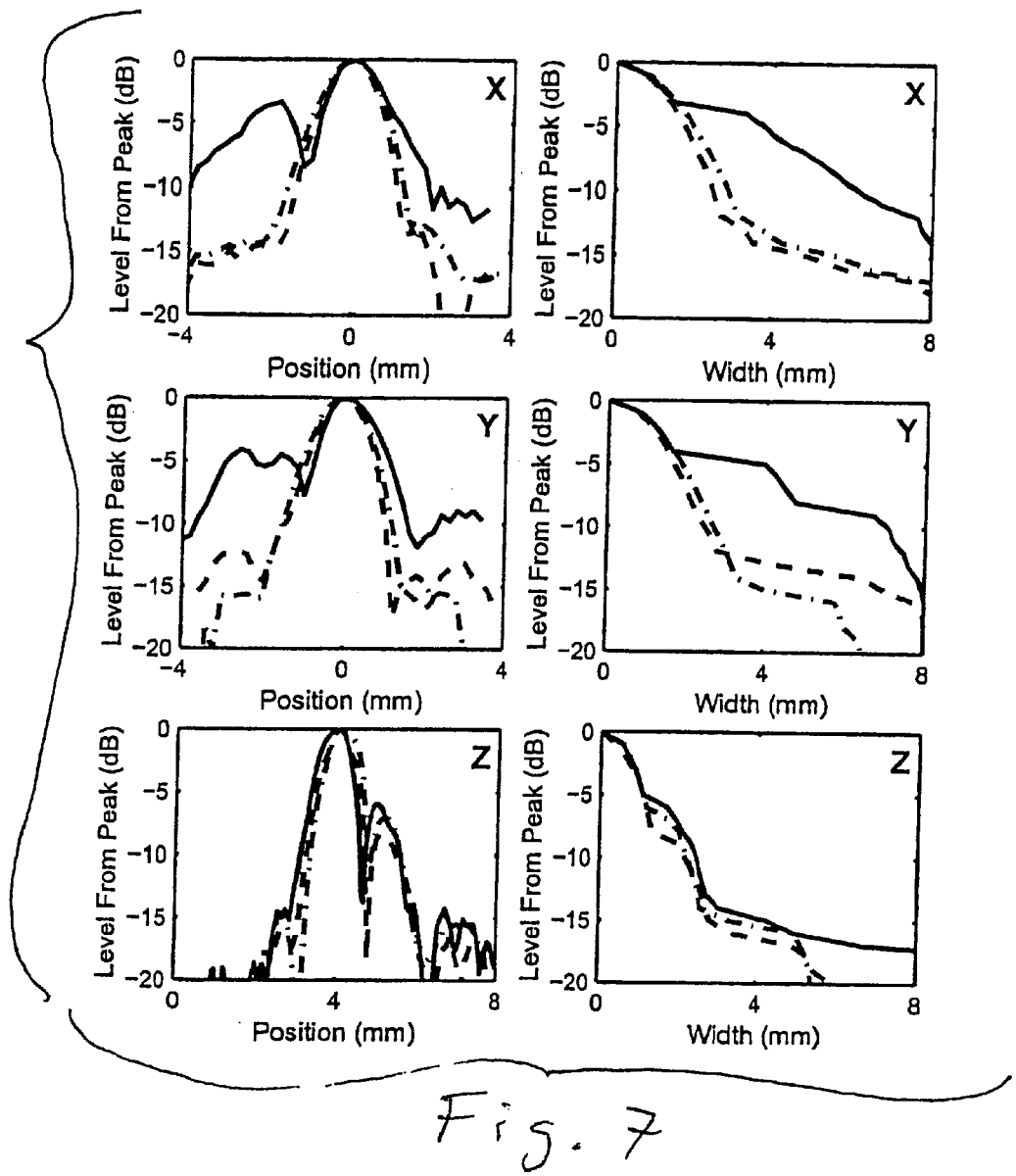
FIG. 7 shows measured cross sections of the transmit focus obtained through an aberrator path.
Figure 8:
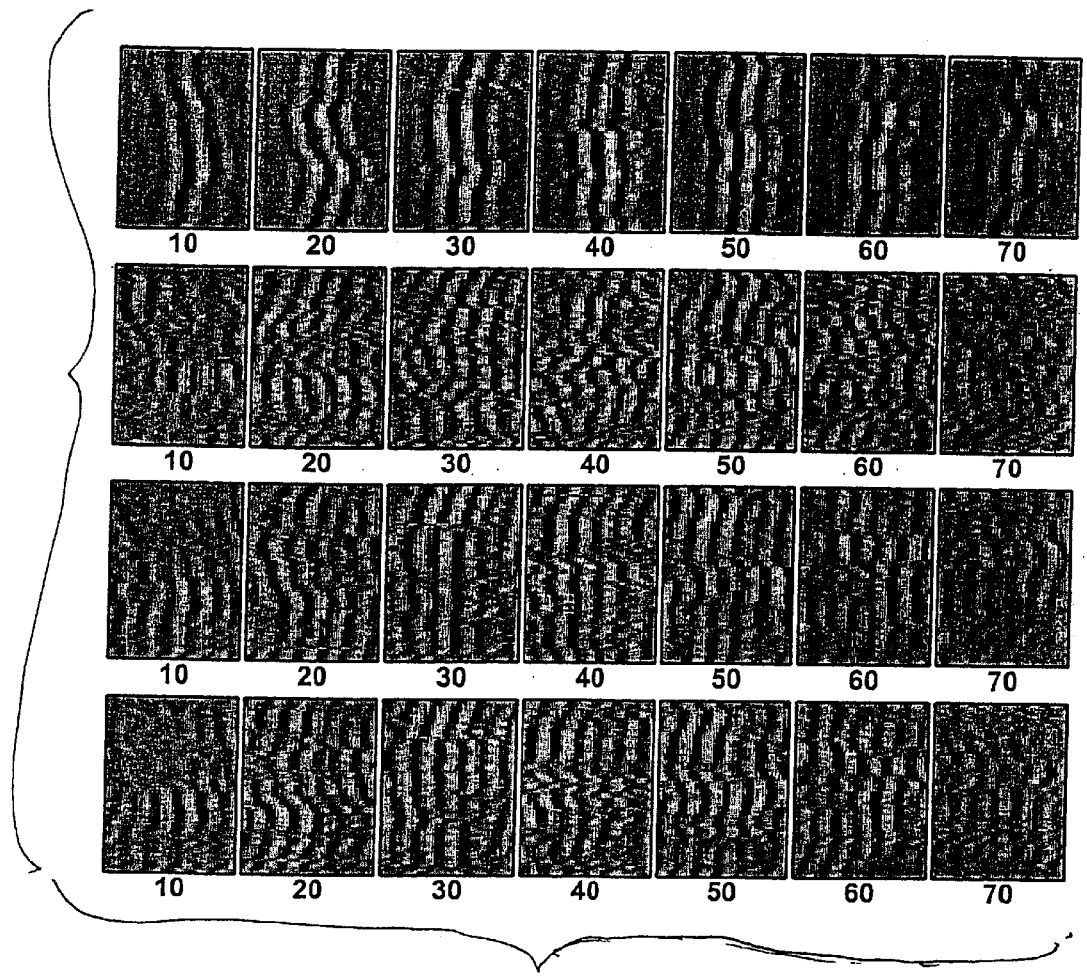
FIG. 8 shows uncompensated waveforms received through the aberrator path.
Figure 9:
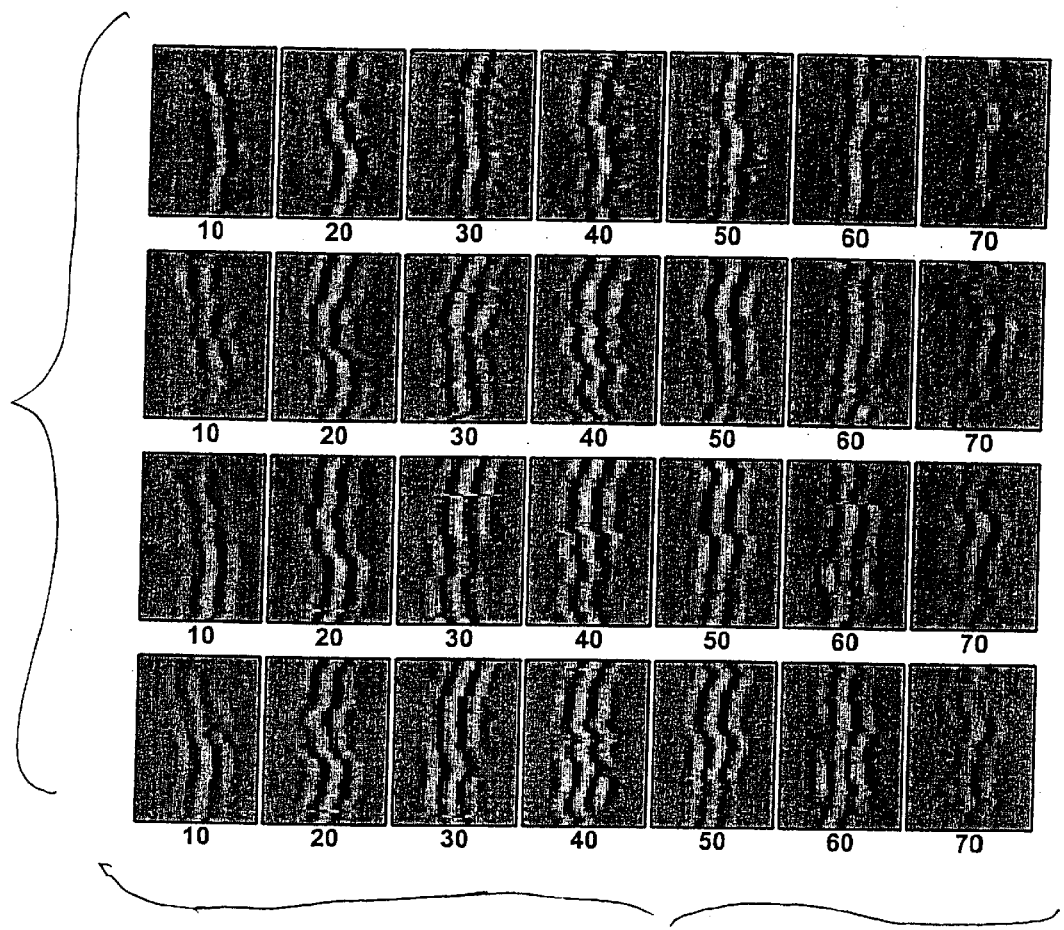
FIG. 9 shows estimated channel responses.

FIG. 4 shows the time history of the receive focus for no compensation, time-shift compensation (TSC), backpropagation followed by time-shift compensation (BP+TSC), and compensation using BSI. The corresponding effective widths in each of three Cartesian dimensions are plotted in FIG. 5 and the associated effective radii are plotted in FIG. 6. Also included in these latter two figures is an ideal case in which every waveform in the aperture is a replication of a pulse that is the result of averaging time-shift compensated receive waveforms. The −10 dB PER for no compensation, TSC, BP+TSC, BSI, and ideal focusing is 0.711, 0.469, 0.421, 0.332, and 0.298, respectively. The data show the uncompensated focus has the poorest resolution. The data also show that, while TSC improved the focus noticeably and BP+TSC improved the focus still further, the BSI method outperformed TSC and BP+TSC significantly by producing a nearly ideal focus down to the −30 dB level. Measured cross sections of the transmit focus obtained through the aberrator are shown in FIG. 7 for no predistortion and for predistortion using TSC and using BSI determined in each case from a point reflector. The central part of the compensated focus in each case is restore down to about −12 dB from the peak. Above this level, the focus produce by the TSC method is slightly narrower than the focus produced by the BSI method. The reason for this is that the time reversed transmit waveforms in the BSI case had a more severe spatial apodization than the time-shift compensate transmit waveforms. Beyond the −12 dB level, the transmit focus produced by the BSI method is slightly better overall than the transmit focus produced by the TSC method. Aberrated receive waveforms from the random medium are shown in FIG. 8 along with corresponding point-reflector waveforms for comparison. Channel responses obtained using BSI with the random medium waveforms are shown in FIG. 9 along with channel responses obtained using the reference waveform method. The order of the FIR filters obtained using the reference waveform method is 22 while the order of the filters obtained using the random medium illumination is 26. Using channel responses from the reference waveform method as true values, the GRMSE for responses from BSI with random-medium illumination obtained with no predistortion, predistortion using BSI from a point reflector, and predistortion using TSC from uncompensated random medium data is 0.511, 0.260, and 0.320, respectively.

The channel responses obtained from the compensated transmit focuses are much closer to the point-reflector result than those from the uncompensated transmit focus and the GRMSE of the estimation obtained using time-shift predistortion is not much greater than the estimation obtained with predistortion using BSI from point-reflector waveforms that theoretically yield the best result.

Figure 10:
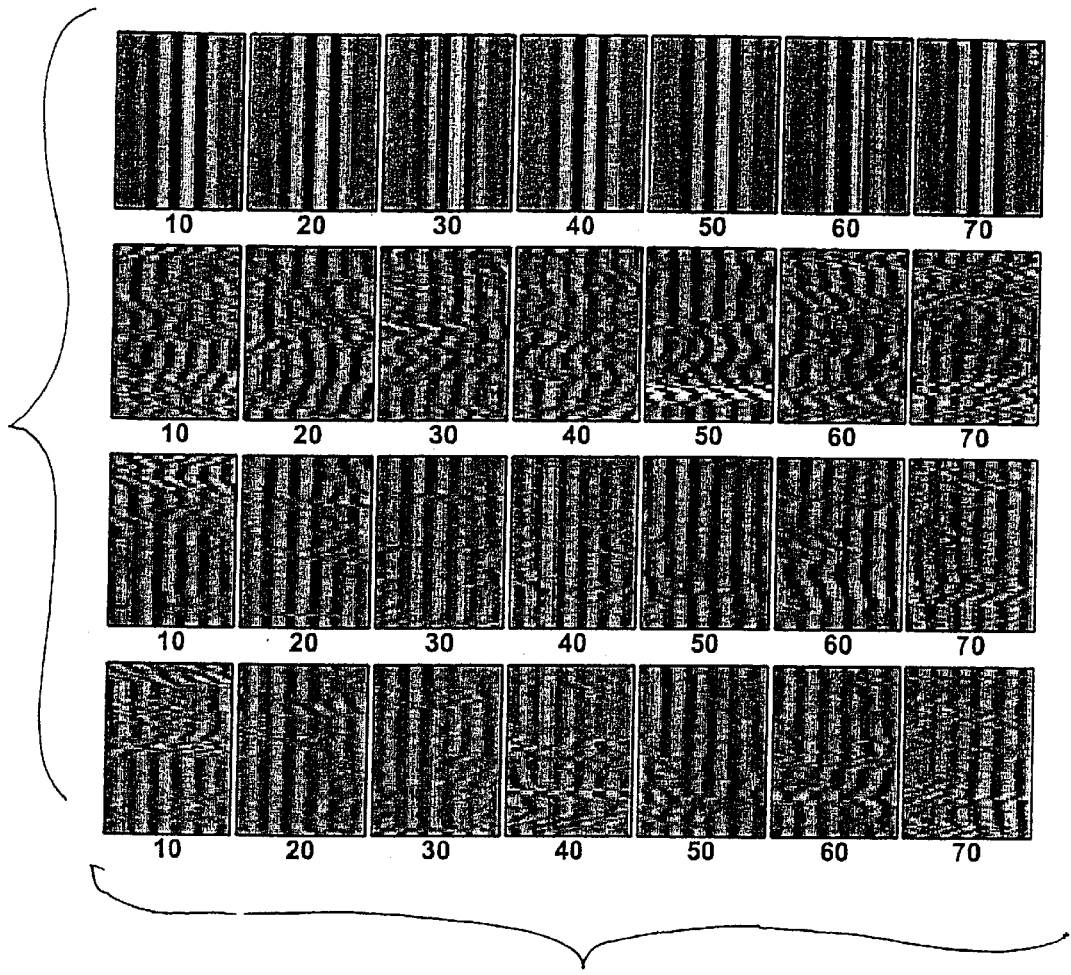
FIG. 10 shows compensated receive waveforms.
Figure 11:
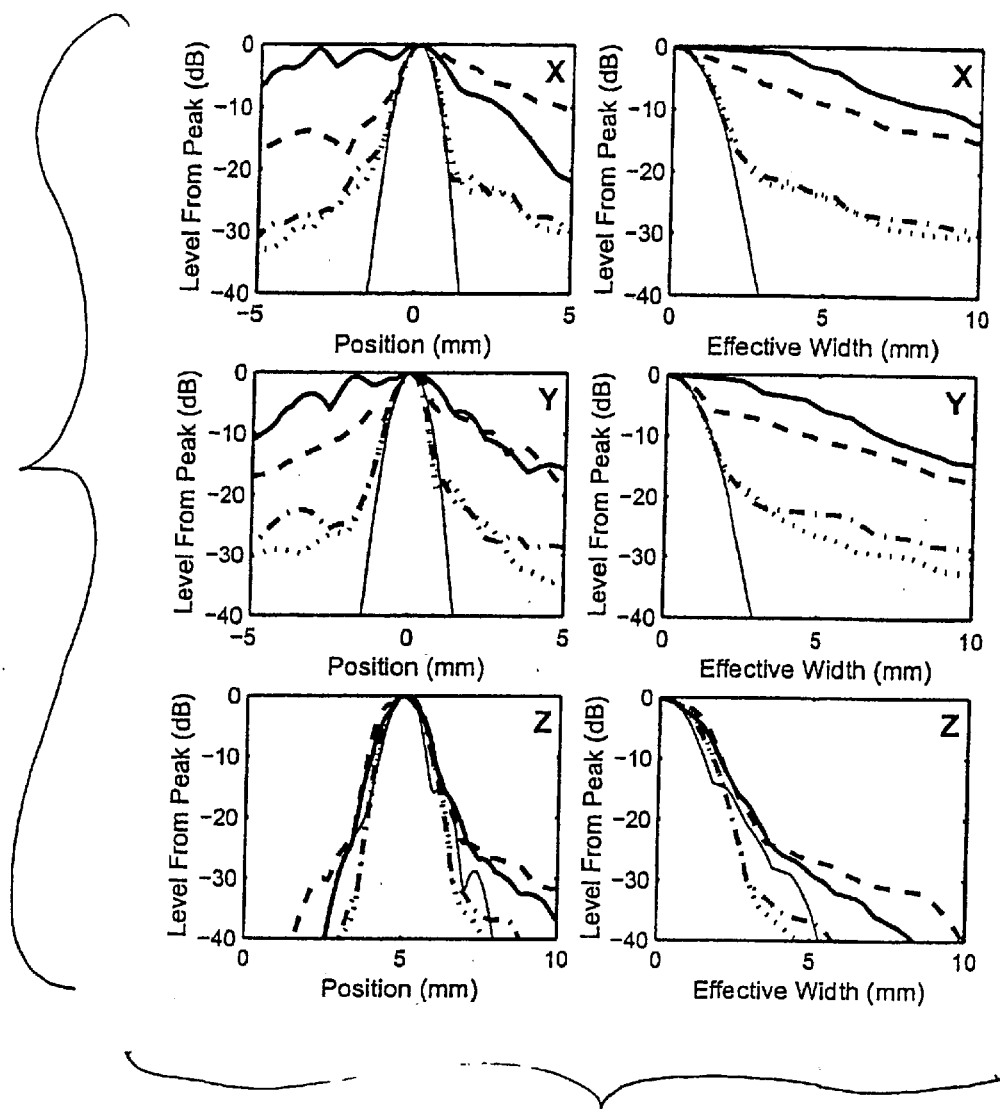
FIG. 11 shows effective widths of the receive focus for random-medium waveforms.
Figure 12:
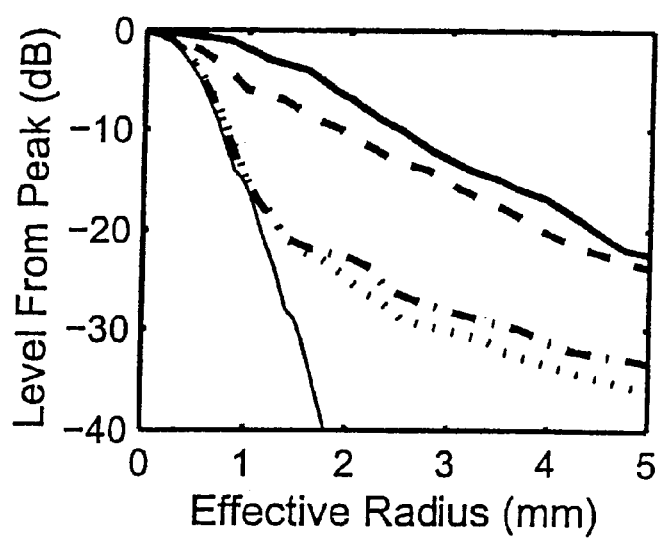
FIG. 12 shows effective radii of the receive focus for random-medium waveforms.

Compensated receive waveforms from the random medium are shown in FIG. 10. While the data indicate BSI compensation may not work well for an uncompensated transmit focus and can even cause divergent results like the bright band shown in the panel numbered 50 in the second row, the data also show BSI compensation base on a transmit focus that has been at least partially compensated does improve the receive wavefront coherence. The resulting effective widths and associated effective radius of the receive focus calculated with a Hamming window applied to the waveforms are shown in FIG. 11 and FIG. 12, respectively.

Figure 13:
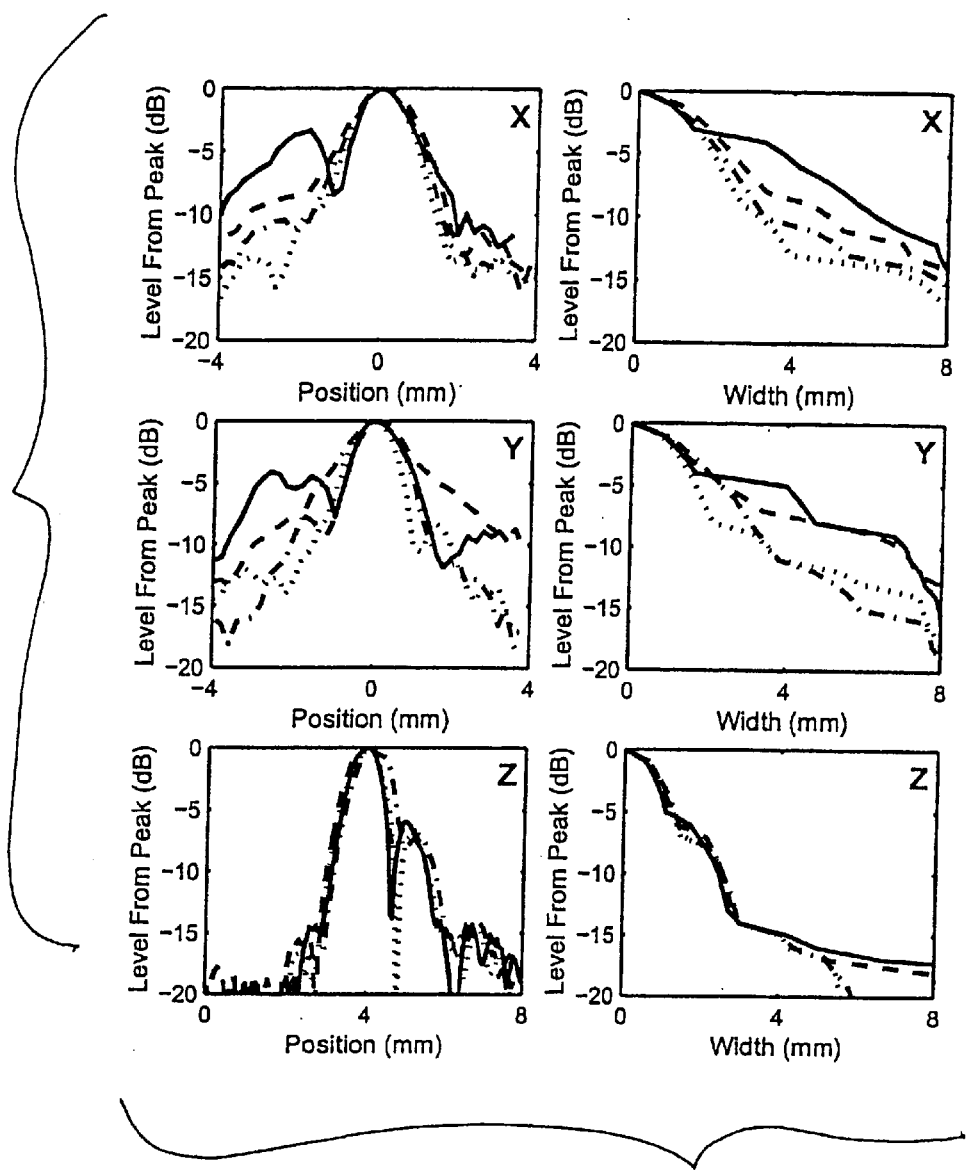
FIG. 13 shows measured cross sections of the compensated transmit focus.

These two figures quantify the effect of the improved coherence. The receive focus in the random medium has been restored down to about −18 dB by BSI using predistorted transmit waveforms. Also, consistent with above values of GRMSE for the corresponding channel responses, predistortion with TSC from an uncompensated transmit focus in the random medium is nearly as effective as predistortion from BSI with point-reflector waveforms. Measured cross sections of the compensated transmit focus produced by BSI from each of three different illuminations are shown in FIG. 13 along with measurements of the aberrated focus before compensation. The transmit focus produced by BSI with predistorted illumination has been restored about the same amount with BSI from TSC as with BSI from point-reflector waveforms. The generally slight increase in the lateral widths of the focus derived from illumination with predistortion using point-reflector waveforms relative to the lateral widths of the focus derive from illumination using TSC is attributed to a stronger spatial apodization of the waveforms receive from the point reflector relative to the apodization of corresponding waveforms receive from the time-shift compensated focus. The data in FIG. 11, FIG. 12, and FIG. 13 indicate that the BSI method of estimation and compensation can yield from random-medium waveforms a significantly improved transmit and receive focus in the presence aberration that has statistics at the high end of those measured for transmission through abdominal wall.

In more detail, the experimental results of FIGS. 3–13 have the following significance:

The experimental results shown in FIGS. 3–13 indicate the following:

FIG. 3: Blind system identification and correction using a point reflector. Each panel shows waveforms as a shade of gray on a bipolar linear scale. The horizontal axis is time and spans 2 $\mu$s. The vertical axis is a 79-element column of the two-dimensional array. Under each panel is the (zero-origin) number of the column for which waveforms are displayed. The first row shows aberrated receive waveforms after correction for geometric path differences. The second row shows corresponding channel responses obtained using BSI. The third row shows corresponding compensated receive waveforms. The fourth row shows corresponding predistorted transmit waveforms.

FIG. 4: Time histories of the receive focus for a point reflector. Each panel shows the amplitude of the focus as a shade of gray on a 50 dB log scale in a 20.4×20.4 mm$^2$ field of the focal plane at an instant of time. The number below each panel is the (zero-origin) time sample in a 256-point time history. The time step between consecutive panels is 0.5 $\mu$s. The array-aberrator configuration is the same as for FIG. 3. The first row shows the receive focus of uncompensated data. The second, third, and fourth row show the corresponding focus after TSC, BP+TSC, and compensation base on BSI, respectively.

Figure 5:
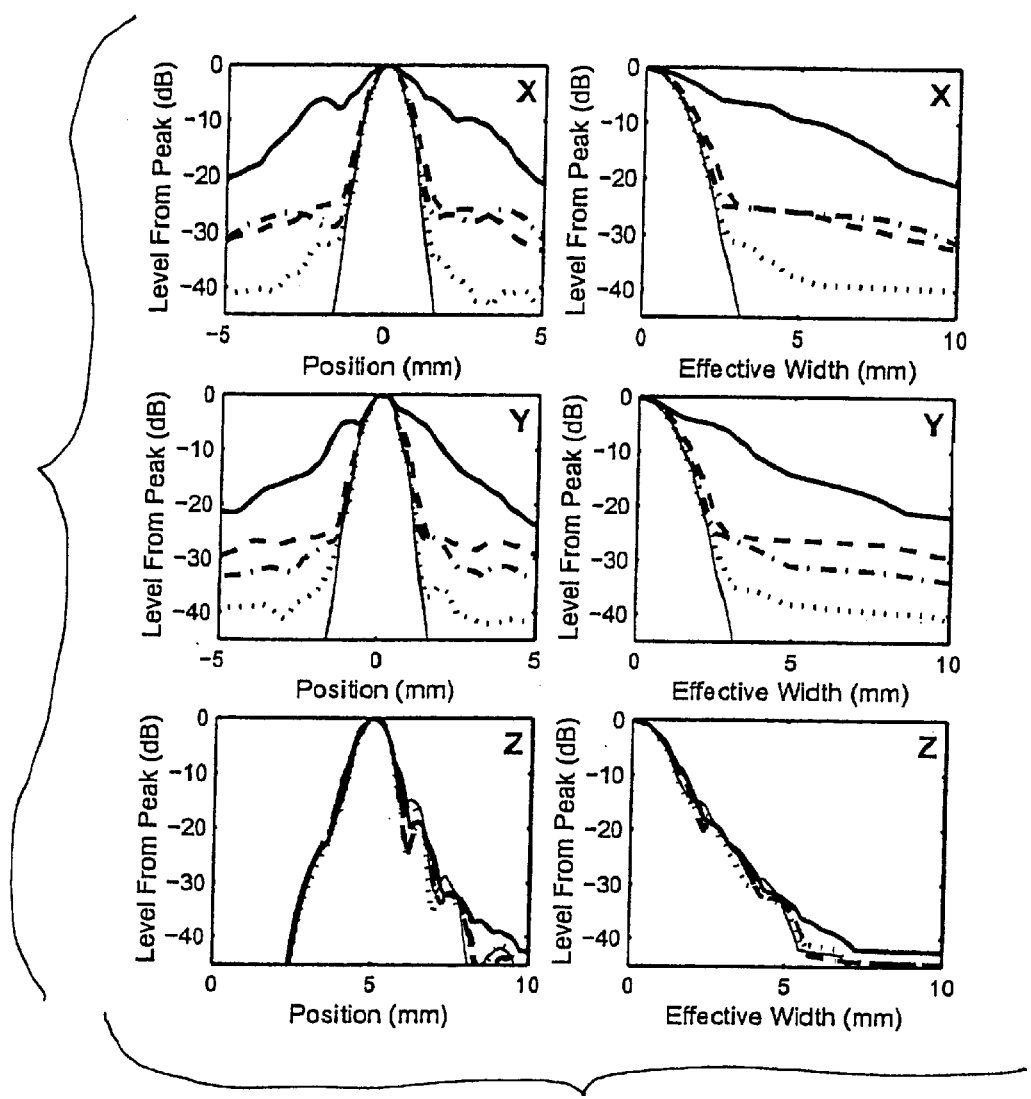
FIG. 5 shows the effective widths corresponding to the time histories of FIG. 4.

FIG. 5: Amplitude projections and effective widths of the receive focus for a point reflector. The left panels show maximum amplitude projections of the focus amplitude in three Cartesian dimensions while the right panels show corresponding effective widths. The upper and middle panels are for the two orthogonal spatial dimensions parallel to the two-dimensional array and the lower panels are for the depth direction. The array-aberrator configuration is the same as for FIG. 3. In each panel, the bold solid line is for no compensation, the dashed line is for TSC, the dash-dot line is for BP+TSC, the dotted line is for compensation based on BSI, and the narrow solid line is for ideal waveforms.

Figure 6:
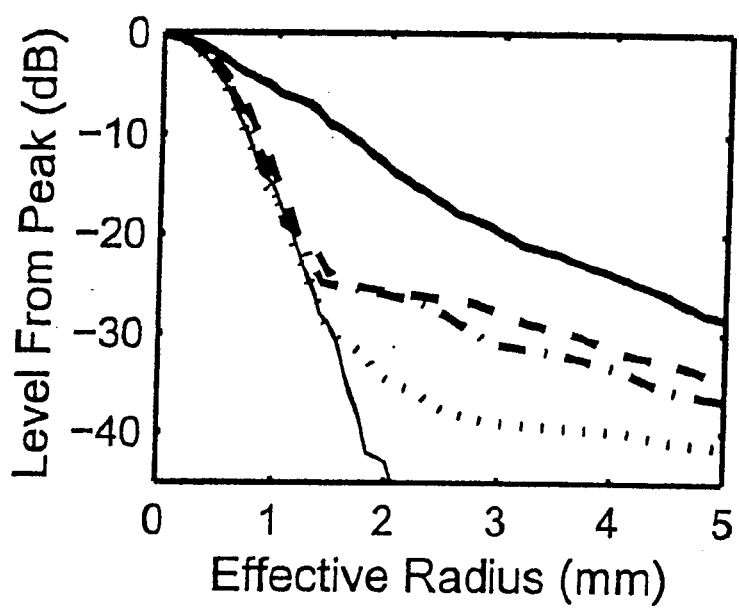
FIG. 6 shows effective radii of the receive focus for the point reflector.

FIG. 6: Effective radii of the receive focus for a point reflector. The curves have the correspondence to cases as in FIG. 5.

FIG. 7: Measured cross sections of the transmit focus obtained through an aberrator path with geometric focusing and with predistortion using point-reflector data. The left panels show cross sections through the peak in each of three Cartesian dimensions and the right panels show corresponding widths. The upper and middle panels are for the two orthogonal spatial dimensions parallel to the two-dimensional array and the lower panels are for the depth direction. The array-aberrator configuration is the same as for FIG. 3. In each panel, the solid line is for an uncompensated (geometric) focus, the dashed line is for predistortion using TSC, and the dash-dot line is for predistortion using BSI.

FIG. 8: Uncompensated waveforms received through an aberrator path. The format and scales are the same as in FIG. 3 and the array-aberrator configuration is the same as for FIG. 3. The first row shows waveforms from the point reflector. The second, third, and fourth row show corresponding waveforms from the random medium in the same position but illuminated with no predistortion, predistortion using BSI from point-reflector waveforms in the first row, and predistortion using TSC from random-medium waveforms in the second row, respectively.

FIG. 9: Estimated channel responses. The format and scales are the same as in FIG. 3 and the array-aberrator configuration is the same as for FIG. 3. The first row shows channel responses obtained using the reference waveform method with point-reflector data. Rows two, three, and four show channel responses obtained using BSI from waveforms in the corresponding three rows of FIG. 8, i.e., waveforms from random medium illumination with no predistortion, predistortion using BSI from point-reflector waveforms, and predistortion using TSC from an uncompensated focus in the random medium, respectively.

FIG. 10: Compensated receive waveforms. The format and scales are the same as in FIG. 3. The first row shows waveforms compensated using channel responses obtained from the reference waveform method with point-reflector data. The second, third, and fourth row show waveforms compensated using channel responses in the corresponding three rows of FIG. 9, i.e., responses from BSI with random medium illumination with no predistortion, predistortion using BSI from point-reflector waveforms, and predistortion using TSC from an uncompensated focus in the random medium, respectively.

FIG. 11: Effective widths of the received focus for random-medium data. As in FIG. 5, the left panels show maximum amplitude projections of the focus amplitude in three Cartesian dimensions while the right panels show corresponding effective widths. The upper and middle panels are for the two orthogonal spatial dimensions parallel to the two-dimensional array, and the lower panels are for the depth direction. In each panel, the bold solid line is for no predistortion and the narrow solid line is for ideal waveforms while the dashed line, dash-dot line, and dotted line are for compensation using channel responses in the second, third, and fourth row, respectively, of FIG. 10, i.e., responses from BSI with random medium illumination with no predistortion, predistortion using BSI from point-reflector waveforms, and predistortion using TSC from an uncompensated focus in the random medium, respectively.

FIG. 12: Effective radii of the receive focus for random-medium data an ideal waveforms. The curves have the same correspondence to cases as in FIG. 11.

FIG. 13: Measured cross sections of the transmit focus for random-medium data. As in FIG. 7, the left panels show cross sections through the peak in each of three Cartesian dimensions and the right panels show corresponding widths. The upper and middle panels are for the two orthogonal spatial dimensions parallel to the two-dimensional array and the lower panels are for the depth direction. The array-aberrator configuration is the same as for FIG. 3. In each panel, the solid line is for no predistortion while the dashed line, dash-dot line, and dotted line are for predistortion using channel responses in the second, third, and fourth row, respectively, of FIG. 9, i.e., responses from BSI with random medium illumination with no predistortion, predistortion using BSI from point-reflector waveforms, and predistortion using TSC from an uncompensated focus in the random medium, respectively.

The common random input filter model provides a general description of propagation through an inhomogeneous medium. Methods that use a single phase screen can be regarded as special cases of the model. In the TSC method, each propagation path is modeled as a delay line. The BP+TSC method is also a special case since backpropagation is a linear process. Both methods have limitations since each of the methods models aberration as being comprised of time shifts in a single plane. The new model is capable of describing more general (distributed) aberration and the performance is limited in principle only by the order of the FIR filters and the validity of the common input assumption. The improvement of the focus obtained with the BSI method is strongly related to the validity of the common input assumption. Aberration correction using the BSI method is best for point-reflector waveforms because the assumption of a common input is almost ideally satisfied. For the aberration and random-medium illumination in this study, the estimation of the channel responses using BSI with uncompensated illumination of a random medium did not yield satisfactory results. In this case, the transmit focus was blurred enough by the aberration that the common source assumption of the BSI method was not sufficiently valid. For the transmit focus from predistortion using TSC with random medium waveforms from an uncompensated focus, the common source was sufficiently well satisfied that the BSI method improved both the receive and transmit focus. This indicates that a satisfactory initial correction can be made.

The spatial coherence of a random waveform field from a common source point is constant after propagation through a homogenous medium to a far-field aperture of observation. In terms of the van Cittert-Zernicke theorem, the common signal is a point source of intensity that has a constant spatial Fourier transform or coherence in the aperture. In practice, however, the common signal is the sum of contributions from randomly positioned scatterers in a finite transmit focal volume. As the angle of incidence in the aperture between the source and the point of observation varies from normal at the center of the aperture, the result of the summation changes and the coherence of the signal decreases from unity. The van Cittert-Zernicke theorem describes this relation in the absence of aberration but no analogous theorem exists for distribute aberration in the propagation path. Although the loss of coherence or equivalently the departure from a common source limits the applicability of the model for a poor transmit focus, the good quality of the aberration estimated from random scattering in this investigation using time-shift compensation on transmit indicates that the mo el can be applied in a practical setting.

In addition to the subspace method, the cross-relation method and the two-step maximum likelihood method were investigated to implement the model for correction of ultrasonic aberration. All of the methods performed well in simulations with a small amount of additive white noise and with the common source assumption perfectly satisfied. The application of the methods to aberration correction is, however, a challenge. First, the number of receive waveform samples is limited because only a small interval around the focus can be used. Samples outside this interval are from scatterers elsewhere and these samples violate the common source assumption. Since only a few samples are used, a reliable statistical average may not be readily obtained. Second, the signal-to-noise ratio may be poor. The noise in the model includes all the nonidealities. Since the transmit focus may not at least initially be small enough, the receive waveforms are the sum of the reflections from a larger than desirable volume and, consequently, the common input assumption may not be sufficiently valid. This is the most important source of noise. Third, the order of the filters needs to be assumed. No satisfactory algorithm was found to estimate the order of the channel responses from channel outputs. The order was, therefore, based on experience. Insensitivity of the BSI algorithm to the changes in the order is desirable. Simulations indicated that the subspace method performs better with short waveforms and high power levels of additive noise and is less sensitive to changes of filter order than the other methods.

A multiple-level structure is necessary in practice for a two-dimensional array to reduce computational requirements. However, in the two-level BSI method employed in this study, the first-level identification equalizes waveforms only within a subaperture; phase and amplitude differences can remain between subapertures. The subaperture results from the first level generally must be adjusted to obtain waveforms relative to the same reference through-out the aperture. Fortunately, since the assumption of a common input may be close to reality within a small subaperture, the first-level identification can be more accurate than a onelevel estimation for the entire aperture when the aperture is large. The second-level identification is, nevertheless, difficult for random-medium data because the common random input assumption is less valid for a large aperture. The nonidealities appear in the channel frequency response as phase and amplitude jumps at the boundaries of subapertures. The purpose of the calculation, adjustment, and spatial smoothing of time shifts between subapertures and the spatial smoothing of amplitude transitions between subapertures is to place the first-level BSI results on a consistent basis for the second level of BSI. A representative calculation showed that the rms of the time shifts between the subapertures was improved from 66.9 ns to 2.6 ns after correction. This indicates the adjustment of time-shift jumps can be accomplished effectively. The improvement of the focus obtained in this study with the BSI method relative to the uncompensated focus and the focus generally obtained with phase screen methods indicates that amplitude jumps can also be reduced effectively. Variations of the two-level implementation of blind system identification described herein are possible. For example, the common signal x in the model of FIG. 2 can be found from the path responses calculated in the second level of blind system identification. The common signal may then be used to deconvolve path responses from the receive signals in the aperture. This approach avoids path response lengthening forced by the convolution of the first-level and the second-level responses.

In general, as already noted, the solution for the channel responses is unique up to a common filter impulse response, i.e., a set of responses obtained by convolving a solution for the channel responses with any common impulse response is also a solution to the problem. Also as noted, if the filters are assumed to have a fixed finite length, the problem becomes a minimization and the solution is unique up to a scale factor that is ±1 for the constraint $\|h\|=1$ used in this study. However, for different measurements with the same aberration, the resultant fixed-length filters may still be different by a common impulse response. This is not a problem in the current application because the main purpose of the aberration correction is to equalize the signal in each channel. The common convolutional response does, however, complicate the evaluation of the results by necessitating the inclusion of a common convolutional factor in the definition of GRMSE.

The aberration path response obtained from the point reflector has a broader bandwidth than the point-like rod reflector response measured in the presence of the aberration. This is shown in FIG. 3 by the shorter time duration of the path response compared to the point response. The main reason for the broader bandwidth of the path response is that the essentially unlimited bandwidth of the path response is limited by convolution primarily with the finite bandwidth measurement system response and to a lesser extent with the finite duration impulse response of the rod reflector. In the method of blind system identification, the broader band path response is recovered throughout the measurement bandwidth where the signal-to-noise is adequate but the effective width in the range or z direction as shown in FIG. 6 is not significantly changed because both the transmitted and receive waveforms are bandwith limited by the system.

The experimental results in this paper were obtained using a unique two-dimensional array system with three capabilities that merit emphasis. First, the two-dimensional array can implement apertures up to 48 mm on each edge. With a 48 mm aperture, the lateral resolution limit, defined as the product of wavelength and f-number, may be improved about an order of magnitude to about 0.6 mm from the few millimeters that is the case in the direction perpendicular to the scan plane imaged by many present clinical instruments. Second, the array is capable of forming square apertures that have the same theoretical resolution in each lateral dimension. Studies have shown that a two-dimensional aperture with a large elevation outperforms a one-dimensional aperture significantly for compensation of aberration. Third, each transmit waveform can be programmed independently. This enables adaptive transmit focusing to produce a sufficiently concentrated effective source that measurements in this paper indicate is required to obtain a satisfactory aberration estimate using BSI with scattering from a random medium. In addition to results reported here for transmit and receive focusing through an aberration with statistics at the high end in the range of those for abdominal wall measurements, trials were made using an aberrator with statistics at the low end of the range for abdominal wall. These trials indicated that the blind system identification method describe here did not require time-shift compensation of the transmit focus to estimate satisfactorily the path response from the focus to the elements in the aperture. The conditions reported here are, therefore, considered to provide a difficult and rigorous test of blind system identification for the estimation of aberration. The correction of arrival time variations in the computational procedure is independent of the BSI algorithm. The correction is used to reduce the order of the channel responses necessary for a satisfactory description of the aberration and to ensure time jumps between subapertures are primarily caused by the nature of the second-level BSI. Since time shifts removed from the waveforms are included in the channel responses later, the accuracy of the correction has only an indirect effect on the BSI.

The two-dimensional 79×79-element aperture was divided into 144 7×7-element square subapertures for first level of the BSI. Although a smaller subaperture would require less computation, smaller subapertures require in practice more levels of BSI and this broadens the estimate channel responses from the convolution step given in Eq. (16). The broadening blurs resolution in depth direction after compensation. Simulations demonstrated that use of more time samples yields better statistics and, hence, more accurate results in the presence of noise. However, in this application, the number of samples is limited by the focal depth. For an f/1.2 focus, the −6 dB transmit-receive focal depth at a frequency of 3 MHz extends over 136 samples for a 20 MHz sampling rate. However, trial calculations with experimental data showed that signals covering approximately 30% of this focal depth, i.e., about 40 samples, yielded the best estimation of the channel responses.

The order of the channel filter at each level needs to be chosen by repeated trials or from experience. The order of the final responses is, as noted, the sum of the order at each level. Basically, the higher the coherence of the data, the smaller the required order of the channel filters for satisfactory compensation. For the measurements in this paper, the filter order at each level was chosen to be 11 for the point-reflector data and 13 for the random-medium data. Trial calculations with other orders showed that the subspace method is not very sensitive to the order changes. Also, BSI results obtained with a fixed order were stable for sets of data with different effective sizes of transmit focus.

The receive and transmit focusing may be corrected in either of two ways. One is an inverse filter method or deconvolution. The other is a matched filter method or time reversal. The transfer functions of each approach have the same phase at each frequency. The difference is their amplitude at each frequency. For receive focusing, to produce uniform amplitude waveforms for beam formation based on the assumption of a homogeneous propagation path, an inverse filter method is desirable. The transmit correction is not so straightforward because the aberration may arise from two sources: diffraction and attenuation. To correct for diffraction in a lossless medium, time reversal is the proper method; to correct for inhomogeneous attenuation in a lossy medium, deconvolution may be better. The choice between these methods is determined by which of the sources is dominant in the aberration. Measurements showed that, for the aberration employed in this study, predistortion using time reversal produced a better transmit focus than predistortion using an inverse filter.

While a preferred embodiment has been set forth above, those skilled in the art who have reviewed the present specification will readily appreciate that other embodiments can be achieved within the scope of the present invention. Various examples of possible variations have been set forth above. In addition, specific numerical values should be construed as illustrative rather than limiting. Further, hardware configurations other than that of FIG. 15 can be used. Therefore, the present invention should be construed as limited only by the appended claims.

We claim:

1. A method of ultrasonic imaging of an object in a path, the method comprising:
   (a) sending transmit signals into the object to produce echoes;
   (b) receiving the echoes and producing raw data signals representing the echoes;
   (c) from the raw data signals, estimating aberration through blind system identification by representing the path as a bank of linear filters; and
   (d) using the aberration estimated in step (c) to apply a compensation to at least one of the transmit signals and the raw data signals to compensate for the aberration.

2. The method of claim 1, wherein step (d) is performed on the transmit signals by using predistortion.

3. The method of claim 1, wherein step (d) is performed on the raw data signals by using deconvolution or an inverse filter method.

4. The method of claim 3, wherein step (b) is performed using a plurality of transducers which define an aperture.

5. The method of claim 4, wherein step (c) comprises:
   (i) grouping the plurality of transducers into a plurality of subapertures;
   (ii) from the raw data signals in each of the subapertures, estimating an aberration response to each transducer through blind system identification;
   (iii) carrying out a deconvolution or inverse filter method to find an input for each of the plurality of subapertures to derive an input for each of the plurality of subapertures;
   (iv) from the input for each of the plurality of subapertures, estimating an aberration response through blind system identification; and
   (v) convolving the response found in step (c)(ii) with the response found in step (c)(iv) to obtain a total aberration response for each transducer in the aperture.

6. The method of claim 5, wherein step (c)(v) comprises:
   (A) carrying out deconvolution or an inverse filter method to find an input for all of the aperture, using the input for each of the plurality of subapertures derived in step (c)(ii) and the response found in step (c)(iv); and
   (B) from the input found in step (c)(v)(A) and the raw data signals for each transducer, estimating a total aberration response through deconvolution or an inverse filter method.

7. The method of claim 5, wherein step (c)(v) comprises:
   (A) using the aberration responses estimated in step (c)(iv) to derive an input for a second level of blind system identification; and
   (B) using the input derived in step (c)(v)(A) and the raw data signals to obtain the total aberration response.

8. The method of claim 5, wherein step (c)(iv) comprises eliminating phase and amplitude jumps among the plurality of subapertures after the convolution.

9. The method of claim 1, wherein step (d) comprises applying a time reversal to obtain a predistortion of the transmit signals.

10. The method of claim 9, wherein step (d) further comprises applying a deconvolution or inverse filter method to obtain a compensation of the raw data signals.

11. The method of claim 1, wherein step (d) comprises applying a compensation to the raw data signals.

12. A system for ultrasonic imaging of an object in a path, the system comprising:
   an ultrasonic transducer system for (i) sending transmit signals into the object to produce echoes and for (ii)

receiving the echoes and producing raw data signals representing the echoes; and circuitry, in communication with the ultrasonic transducer system to receive the raw data signals, for (i) estimating from the raw data signals, an aberration through blind system identification by representing the path as a bank of linear filters, and (ii) using the estimated aberration to apply a compensation to at least one of the transmit signals and the raw data signals to compensate for the aberration.

13. The system of claim 12, wherein the circuitry applies the compensation to the transmit signals by using predistortion.

14. The system of claim 12, wherein the circuitry applies the compensation to the raw data signals by deconvolution or using an inverse filter method.

15. The system of claim 14, wherein the ultrasonic transducer system comprises a plurality of transducers which define an aperture.

16. The system of claim 15, wherein the circuitry estimates the aberration by:

(i) grouping the plurality of transducers into a plurality of subapertures;

(ii) from the raw data signals in each of the subapertures, estimating an aberration response to each transducer through blind system identification;

(iii) carrying out a deconvolution or inverse filter method to find an input for each of the plurality of subapertures to derive an input for each of the plurality of subapertures;

(iv) from the input for each of the plurality of subapertures, estimating an aberration response through blind system identification; and (v) convolving the response found in step (ii) with the response found in step (iv) to obtain a total aberration response for each transducer in the aperture.

17. The system of claim 16, wherein the circuitry performs step (v) by:

(A) carrying out deconvolution or an inverse filter method to find an input for all of the aperture, using the input for each of the plurality of subapertures derived in step (ii) and the response found in step (iv); and (B) from the input found in step (v)(A) and the raw data signals for each transducer, estimating a total aberration response through deconvolution or an inverse filter method.

18. The system of claim 16, wherein the circuitry performs step (v) by:

(A) using the aberration responses estimated in step (iv) to derive an input for a second level of blind system identification; and (B) using the input derived in step (v)(A) and the raw data signals to obtain the total aberration response.

19. The system of claim 16, wherein the circuitry performs step (iii) by eliminating phase and amplitude jumps among the plurality of subapertures.

20. The system of claim 12, wherein the circuitry applies time reversal to obtain a predistortion of the transmit signals.

21. The system of claim 20, wherein the circuitry applies a deconvolution or an inverse filter method to obtain a compensation of the raw data signals.

22. The system of claim 12, wherein the circuitry applies deconvolution or an inverse filter method to obtain a compensation of the raw data signals.

23. The system of claim 12, wherein the ultrasonic transducer system comprises an array of transducers.

24. The system of claim 23, wherein each of the ultrasonic transducers is a transmit and receive transducer.

* * * * *